(12) United States Patent
Kim et al.

(10) Patent No.: US 11,118,202 B2
(45) Date of Patent: *Sep. 14, 2021

(54) METHOD FOR PURIFYING AND OBTAINING 3,6-ANHYDRO-L-GALACTOSE USING MICROORGANISMS

(71) Applicant: KOREA UNIVERSITY RESEARCH AND BUSINESS FOUNDATION, Seoul (KR)

(72) Inventors: Kyoung Heon Kim, Seoul (KR); In-Geol Choi, Seoul (KR); Sora Yu, Namyangju-si (KR); Eun-Ju Yun, Seoul (KR); Kyung-mun Cho, Seongnam-si (KR)

(73) Assignee: Korea University Research and Business Foundation, Seoul (KR)

( * ) Notice: Subject to any disclaimer, the term of this patent is extended or adjusted under 35 U.S.C. 154(b) by 156 days.

This patent is subject to a terminal disclaimer.

(21) Appl. No.: 16/084,144

(22) PCT Filed: Mar. 31, 2017

(86) PCT No.: PCT/KR2017/003557
§ 371 (c)(1),
(2) Date: Sep. 11, 2018

(87) PCT Pub. No.: WO2017/176010
PCT Pub. Date: Oct. 12, 2017

(65) Prior Publication Data
US 2020/0165646 A1    May 28, 2020

(30) Foreign Application Priority Data
Apr. 4, 2016   (KR) .................. 10-2016-0041058

(51) Int. Cl.
*C12P 19/02*    (2006.01)

(52) U.S. Cl.
CPC ....... *C12P 19/02* (2013.01); *C12Y 302/01081* (2013.01); *C12Y 302/01159* (2013.01)

(58) Field of Classification Search
None
See application file for complete search history.

(56) References Cited

U.S. PATENT DOCUMENTS 9,297,000 B2 * 3/2016 Choi .................. C12N 9/2402
9,902,983 B2 * 2/2018 Kim ............... C12Y 302/01082
10,655,118 B2 * 5/2020 Kim ......................... C12P 19/14
2009/0053776 A1 * 2/2009 Hutcheson ............ C12P 17/162
435/100
2015/0216778 A1   8/2015 Kim et al.

FOREIGN PATENT DOCUMENTS

| KR | 10-2013-0085017 A | 7/2013 |
| KR | 10-1476047 B1 | 12/2014 |
| KR | 10-2015-0016006 A | 2/2015 |
| KR | 10-1489732 B1 | 2/2015 |
| WO | WO-2010099153 A2 * | 9/2010 ............... A61P 7/00 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession Q21LJ2. Apr. 18, 2006 (Year: 2006).*
Accession Q21HC5. Apr. 18, 2006 (Year: 2006).*
Accession Q21HB2. Apr. 18, 2006. (Year: 2006).*
Liu et al. Biotechnol Appl Biochem. Mar.-Apr. 2016;63(2):230-7. Epub May 24, 2015. (Year: 2015).*
Escalante-Chong et al. Proc Natl Acad Sci U S A. Feb. 3, 2015; 112(5): 1636-1641. (Year: 2015).*
Yanase et al. Appl Microbiol Biotechnol (1991) 35:364-368 (Year: 1991).*
Hwang, Hyeong Jin, et al., "Fermentation of Seaweed Sugars by *Lactobacillus* Species and the Potential of Seaweed as a Biomass Feedstock", *Biotechnology and Bioprocess Engineering*, Jul. 2, 2011, vol. 16, pp. 1231-1239 (9 pages in English).
Kim, Hee Taek, et al., "The complete enzymatic saccharification of agarose and its application to simultaneous saccharification and fermentation of agarose for ethanol production", *Bioresource Technology*, Dec. 6, 2011, vol. 107, pp. 301-306 (6 pages in English).
Saccharophagus degradans, "agarose [*Saccharophagus degradans*]", NCBI Reference Sequence: WP_011467657.1, Jul. 11, 2013, pp. 1-2 (3 pages in English).
International Search Report dated Jun. 30, 2017 in International Application No. PCT/KR2017/003557 (2 pages in English, 2 pages in Korean).
"Agarase precursor", *NCBI*, https://www.ncbi.nlm.nih.gov/protein/Q21LJ2 (2 pages in English).
Chinese Office Action dated Dec. 4, 2020 in counterpart Chinese Application No. 201780021204.5 (9 pages in Chinese).

* cited by examiner

*Primary Examiner* — Christian L Fronda
(74) *Attorney, Agent, or Firm* — NSIP Law

(57) ABSTRACT

The present invention relates to a novel method for purifying 3,6-anhydro-L-galactose by using microorganisms and provides an effect of improving the production yield of 3,6-anhydro-L-galactose by using microorganisms during purification after enzymatic hydrolysis of agarose or agar.

2 Claims, 7 Drawing Sheets

Specification includes a Sequence Listing.

SEQUENCE LISTING

<160> NUMBER OF SEQ ID NOS: 4

<210> SEQ ID NO 1

<211> LENGTH: 598
<212> TYPE: PRT
<213> ORGANISM: Saccharophagus degradans 2-40

<400> SEQUENCE: 1

```
Met Lys Thr Thr Lys Cys Ala Leu Ala Ala Leu Phe Phe Ser Thr Pro
1               5                   10                  15

Leu Met Ala Ala Asp Trp Asp Gly Ile Pro Val Pro Ala Asp Pro Gly
            20                  25                  30

Asn Gly Asn Thr Trp Glu Leu Gln Ser Leu Ser Asp Phe Asn Tyr
        35                  40                  45

Ala Ala Pro Ala Asn Gly Lys Ser Thr Thr Phe Tyr Ser Arg Trp Ser
50                  55                  60

Glu Gly Phe Ile Asn Ala Trp Leu Gly Pro Gly Gln Thr Glu Phe Tyr
65                  70                  75                  80

Gly Pro Asn Ala Ser Val Glu Gly Gly His Leu Ile Ile Lys Ala Thr
                85                  90                  95

Arg Lys Pro Gly Thr Thr Gln Ile Tyr Thr Gly Ala Ile His Ser Asn
            100                 105                 110

Glu Ser Phe Thr Tyr Pro Leu Tyr Leu Glu Ala Arg Thr Lys Ile Thr
        115                 120                 125

Asn Leu Thr Leu Ala Asn Ala Phe Trp Leu Leu Ser Ser Asp Ser Thr
130                 135                 140

Glu Glu Ile Asp Val Leu Glu Ser Tyr Gly Ser Asp Arg Ala Thr Glu
145                 150                 155                 160

Thr Trp Phe Asp Glu Arg Leu His Leu Ser His His Val Phe Ile Arg
                165                 170                 175

Gln Pro Phe Gln Asp Tyr Gln Pro Lys Asp Ala Gly Ser Trp Tyr Pro
            180                 185                 190

Asn Pro Asp Gly Gly Thr Trp Arg Asp Gln Phe Phe Arg Ile Gly Val
        195                 200                 205

Tyr Trp Ile Asp Pro Trp Thr Leu Glu Tyr Tyr Val Asn Gly Glu Leu
210                 215                 220

Val Arg Thr Val Ser Gly Pro Glu Met Ile Asp Pro Tyr Gly Tyr Thr
225                 230                 235                 240

Asn Gly Thr Gly Leu Ser Lys Pro Met Gln Val Ile Phe Asp Ala Glu
                245                 250                 255

His Gln Pro Trp Arg Asp Glu Gln Gly Thr Ala Pro Pro Thr Asp Ala
            260                 265                 270

Glu Leu Ala Asp Ser Ser Arg Asn Gln Phe Leu Ile Asp Trp Val Arg
        275                 280                 285

Phe Tyr Lys Pro Val Ala Ser Asn Asn Gly Gly Gly Asp Pro Gly Asn
290                 295                 300

Gly Gly Thr Pro Gly Asn Gly Ser Gly Asp Thr Val Val Val Glu
305                 310                 315                 320

Met Ala Asn Phe Ser Ala Thr Gly Lys Glu Gly Ser Ala Val Ala Gly
                325                 330                 335

Asp Thr Phe Thr Gly Phe Asn Pro Ser Gly Ala Asn Asn Ile Asn Tyr
            340                 345                 350

Asn Thr Leu Gly Asp Trp Ala Asp Tyr Thr Val Asn Phe Pro Ala Ala
        355                 360                 365

Gly Asn Tyr Thr Val Asn Leu Ile Ala Ala Ser Pro Val Thr Ser Gly
370                 375                 380

Leu Gly Ala Asp Ile Leu Val Asp Ser Ser Tyr Ala Gly Thr Ile Pro
```

```
                385                 390                 395                 400
Val Ser Ser Thr Gly Ala Trp Glu Ile Tyr Asn Thr Phe Ser Leu Pro
                    405                 410                 415

Ser Ser Ile Tyr Ile Ala Ser Ala Gly Asn His Thr Ile Arg Val Gln
                    420                 425                 430

Ser Ser Gly Gly Ser Ala Trp Gln Trp Asn Gly Asp Glu Leu Arg Phe
                    435                 440                 445

Thr Gln Thr Asp Ala Asp Thr Gly Thr Asn Pro Pro Ser Thr Ala Ser
                    450                 455                 460

Ile Ala Val Glu Ala Glu Asn Phe Asn Ala Val Gly Gly Thr Phe Ser
465                 470                 475                 480

Asp Gly Gln Ala Gln Pro Val Ser Val Tyr Thr Val Asn Gly Asn Thr
                        485                 490                 495

Ala Ile Asn Tyr Val Asn Gln Gly Asp Tyr Ala Asp Tyr Thr Ile Ala
                    500                 505                 510

Val Ala Gln Ala Gly Asn Tyr Thr Ile Ser Tyr Gln Ala Gly Ser Gly
                    515                 520                 525

Val Thr Gly Gly Ser Ile Glu Phe Leu Val Asn Glu Asn Gly Ser Trp
                    530                 535                 540

Ala Ser Lys Thr Val Thr Ala Val Pro Asn Gln Gly Trp Asp Asn Phe
545                 550                 555                 560

Gln Pro Leu Asn Gly Gly Ser Val Tyr Leu Ser Ala Gly Thr His Gln
                    565                 570                 575

Val Arg Leu His Gly Ala Gly Ser Asn Asn Trp Gln Trp Asn Leu Asp
                    580                 585                 590

Lys Phe Thr Leu Ser Asn
                    595

<210> SEQ ID NO 2
<211> LENGTH: 1797
<212> TYPE: DNA
<213> ORGANISM: Saccharophagus degradans 2-40

<400> SEQUENCE: 2
atgaaaacca ccaaatgcgc cctagctgcg ctcttcttca gtaccctct tatggctgca      60 gattgggacg gaattcctgt cccagcggac ccagggaatg caacacctg ggagctacag     120 tccctttctg acgatttcaa ctatgcggcc cagctaacg gcaaaagcac caccttctat     180
agccgctgga gcgaaggctt tatcaatgct ggctcggcc ggggcaaac cgagttttac     240 ggccccaatg cttcggtaga aggcggccac cttattatta aggccactcg caagccaggt    300
actactcaaa tttacactgg agcaattcac tccaatgaaa gttttaccta cccattgtat    360
ttggaagcgc gcaccaaaat tacaaacctc accctcgcca acgcatttg gctactaagc    420 tcagattcca ccgaagagat tgatgtgctg agtcttacg gcagcgaccg tgcaacagaa    480
acgtggtttg acgaacgcct acacttaagc catcacgttt ttatccgcca gccatttcaa    540
gactaccaac cgaaagatgc aggcagctgg taccccaacc ccgatggcgg cacttggcgc    600
gaccaatttt tccgtatagg tgtttattgg atagacccat ggacactgga gtattacgtg    660
aatggcgaat tagtgcgcac tgtaagcggc ccagaaatga ttgacccgta cggttacacc    720
aacggcacag gcctaagtaa acccatgcaa gttatttcg atgcagagca tcagccttgg    780
cgcgacgaac aaggtactgc cccacccacc gacgcagagc tagccgactc gagtcgcaat    840
caattcttaa ttgactgggt gcgattctac aaacccgtgg caagcaacaa tggtggcggc    900
```

```
gacccaggca atggcggcac cccaggtaat ggtggcagtg gcgatactgt agtggtagaa    960
atggccaact tctctgccac aggtaaagaa ggctctgcag ttgcaggcga cactttcaca   1020
ggcttcaacc ccagcggcgc gaacaacatc aactacaaca ccttagggga ttgggcagac   1080
tacacggtga acttccccgc tgccggtaat tacaccgtaa acctaattgc agcctcgccg   1140
gttacatctg gctgggtgc agatattttg gtagacagca gttacgcagg caccatacct    1200
gttagcagca ccggagcttg ggagatatac aacaccttta gcttgcccag ctcgatttat   1260
atcgcaagcg caggcaatca tactattcgc gtacaaagct ccggcggtag cgcttggcag   1320
tggaacggcg acgaacttcg ctttacccaa acggatgcgg atacaggcac caatccaccc   1380
agtacagcca gcatagcggt tgaagccgaa aactttaacg cggtgggcgg cacctttagc   1440
gatggtcaag ctcaacctgt tagcgtttac accgttaacg caacactgc cattaactac    1500
gtaaaccaag gcgattatgc cgactacacc attgctgttg cccaagcggg taactacacc   1560
attagctatc aagctggcag tggcgtaaca ggtggtagca tagagttttt ggttaacgaa   1620
aacggaagct gggccagtaa aaccgttacc gccgtaccaa accaaggttg ggataacttc   1680
caacccttaa acggaggcag cgtttaccta agcgcaggca cccaccaagt tcgtttacac   1740
ggcgctggca gcaacaactg gcagtggaac ctagataagt tcacgcttag caactaa      1797
```

<210> SEQ ID NO 3
<211> LENGTH: 747
<212> TYPE: PRT
<213> ORGANISM: Saccharophagus degradans 2-40

<400> SEQUENCE: 3

```
Met Leu Phe Asp Phe Glu Asn Asp Gln Val Pro Ser Asn Ile His Phe
1               5                   10                  15

Leu Asn Ala Arg Ala Ser Ile Glu Thr Tyr Thr Gly Ile Asn Gly Glu
            20                  25                  30

Pro Ser Lys Gly Leu Lys Leu Ala Met Gln Ser Lys Gln His Ser Tyr
        35                  40                  45

Thr Gly Leu Ala Ile Val Pro Glu Gln Pro Trp Asp Trp Ser Glu Phe
    50                  55                  60

Thr Ser Ala Ser Leu Tyr Phe Asp Ile Val Ser Val Gly Asp His Ser
65                  70                  75                  80

Thr Gln Phe Tyr Leu Asp Val Thr Asp Gln Asn Gly Ala Val Phe Thr
                85                  90                  95

Arg Ser Ile Asp Ile Pro Val Gly Lys Met Gln Ser Tyr Tyr Ala Lys
            100                 105                 110

Leu Ser Gly His Asp Leu Glu Val Pro Asp Ser Gly Asp Val Asn Asp
        115                 120                 125

Leu Asn Leu Ala Ser Gly Leu Arg Ser Asn Pro Pro Thr Trp Thr Ser
    130                 135                 140

Asp Asp Arg Gln Phe Val Trp Met Trp Gly Val Lys Asn Leu Asp Leu
145                 150                 155                 160

Ser Gly Ile Ala Lys Ile Ser Leu Ser Val Gln Ser Ala Met His Asp
                165                 170                 175

Lys Thr Val Ile Ile Asp Asn Ile Arg Ile Gln Pro Asn Pro Pro Gln
            180                 185                 190

Asp Glu Asn Phe Leu Val Gly Leu Val Asp Glu Phe Gly Gln Asn Ala
        195                 200                 205

Lys Val Asp Tyr Lys Gly Lys Ile His Ser Leu Glu Glu Leu His Ala
    210                 215                 220
```

-continued

Ala Arg Asp Val Glu Leu Ala Glu Leu Asp Gly Lys Pro Met Pro Ser
225                 230                 235                 240

Arg Ser Lys Phe Gly Gly Trp Leu Ala Gly Pro Lys Leu Lys Ala Thr
            245                 250                 255

Gly Tyr Phe Arg Thr Glu Lys Ile Asn Gly Lys Trp Met Leu Val Asp
        260                 265                 270

Pro Glu Gly Tyr Pro Tyr Phe Ala Thr Gly Leu Asp Ile Ile Arg Leu
    275                 280                 285

Ser Asn Ser Ser Thr Met Thr Gly Tyr Asp Tyr Asp Gln Ala Thr Val
290                 295                 300

Ala Gln Arg Ser Ala Asp Asp Val Thr Pro Glu Asp Ser Lys Gly Leu
305                 310                 315                 320

Met Ala Val Ser Glu Lys Ser Phe Ala Thr Arg His Leu Ala Ser Pro
            325                 330                 335

Thr Arg Ala Ala Met Phe Asn Trp Leu Pro Asp Tyr Asp His Pro Leu
        340                 345                 350

Ala Asn His Tyr Asn Tyr Arg Arg Ser Ala His Ser Gly Pro Leu Lys
    355                 360                 365

Arg Gly Glu Ala Tyr Ser Phe Tyr Ser Ala Asn Leu Glu Arg Lys Tyr
370                 375                 380

Gly Glu Thr Tyr Pro Gly Ser Tyr Leu Asp Lys Trp Arg Glu Val Thr
385                 390                 395                 400

Val Asp Arg Met Leu Asn Trp Gly Phe Thr Ser Leu Gly Asn Trp Thr
            405                 410                 415

Asp Pro Ala Tyr Tyr Asp Asn Asn Arg Ile Pro Phe Phe Ala Asn Gly
        420                 425                 430

Trp Val Ile Gly Asp Phe Lys Thr Val Ser Ser Gly Ala Asp Phe Trp
    435                 440                 445

Gly Ala Met Pro Asp Val Phe Asp Pro Glu Phe Lys Val Arg Ala Met
450                 455                 460

Glu Thr Ala Arg Val Val Ser Glu Glu Ile Lys Asn Ser Pro Trp Cys
465                 470                 475                 480

Val Gly Val Phe Ile Asp Asn Glu Lys Ser Phe Gly Arg Pro Asp Ser
            485                 490                 495

Asp Lys Ala Gln Tyr Gly Ile Pro Ile His Thr Leu Gly Arg Pro Ser
        500                 505                 510

Glu Gly Val Pro Thr Arg Gln Ala Phe Ser Lys Leu Leu Lys Ala Lys
    515                 520                 525

Tyr Lys Thr Ile Ala Ala Leu Asn Asn Ala Trp Gly Leu Lys Leu Ser
530                 535                 540

Ser Trp Ala Glu Phe Asp Leu Gly Val Asp Val Lys Ala Leu Pro Val
545                 550                 555                 560

Thr Asp Thr Leu Arg Ala Asp Tyr Ser Met Leu Leu Ser Ala Tyr Ala
            565                 570                 575

Asp Gln Tyr Phe Lys Val Val His Gly Ala Val Glu His Tyr Met Pro
        580                 585                 590

Asn His Leu Tyr Leu Gly Ala Arg Phe Pro Asp Trp Gly Met Pro Met
    595                 600                 605

Glu Val Val Lys Ala Ala Lys Tyr Ala Asp Val Val Ser Tyr Asn
610                 615                 620

Ser Tyr Lys Glu Gly Leu Pro Lys Gln Lys Trp Ala Phe Leu Ala Glu
625                 630                 635                 640

```
Leu Asp Lys Pro Ser Ile Ile Gly Glu Phe His Ile Gly Ala Met Asp
                645                 650                 655

His Gly Ser Tyr His Pro Gly Leu Ile His Ala Ala Ser Gln Ala Asp
            660                 665                 670

Arg Gly Glu Met Tyr Lys Asp Tyr Met Gln Ser Val Ile Asp Asn Pro
        675                 680                 685

Tyr Phe Val Gly Ala His Trp Phe Gln Tyr Met Asp Ser Pro Leu Thr
    690                 695                 700

Gly Arg Ala Tyr Asp Gly Glu Asn Tyr Asn Val Gly Phe Val Asp Val
705                 710                 715                 720

Thr Asp Thr Pro Tyr Gln Glu Met Val Asp Ala Ala Lys Glu Val Asn
                725                 730                 735

Ala Lys Ile Tyr Thr Glu Arg Leu Gly Ser Lys
                740                 745

<210> SEQ ID NO 4
<211> LENGTH: 368
<212> TYPE: PRT
<213> ORGANISM: Saccharophagus degradans 2-40

<400> SEQUENCE: 4

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
            20                  25                  30

Phe Asp Ile Thr Pro Leu Lys Gly Asp Leu Ala Tyr Glu Glu Gly Val
        35                  40                  45

Ile Arg Arg Asp Pro Ser Ala Val Leu Lys Val Asp Asp Glu Tyr His
    50                  55                  60

Val Trp Tyr Thr Lys Gly Glu Gly Glu Thr Val Gly Phe Gly Ser Asp
65                  70                  75                  80

Asn Pro Glu Asp Lys Val Phe Pro Trp Asp Lys Thr Glu Val Trp His
                85                  90                  95

Ala Thr Ser Lys Asp Lys Ile Thr Trp Lys Glu Ile Gly Pro Ala Ile
            100                 105                 110

Gln Arg Gly Ala Ala Gly Ala Tyr Asp Asp Arg Ala Val Phe Thr Pro
        115                 120                 125

Glu Val Leu Arg His Asn Gly Thr Tyr Tyr Leu Val Tyr Gln Thr Val
    130                 135                 140

Lys Ala Pro Tyr Leu Asn Arg Ser Leu Glu His Ile Ala Ile Ala Tyr
145                 150                 155                 160

Ser Asp Ser Pro Phe Gly Pro Trp Thr Lys Ser Asp Ala Pro Ile Leu
                165                 170                 175

Ser Pro Glu Asn Asp Gly Val Trp Asp Thr Asp Glu Asp Asn Arg Phe
            180                 185                 190

Leu Val Lys Glu Lys Gly Ser Phe Asp Ser His Lys Val His Asp Pro
        195                 200                 205

Cys Leu Met Phe Phe Asn Asn Arg Phe Tyr Leu Tyr Tyr Lys Gly Glu
    210                 215                 220

Thr Met Gly Glu Ser Met Asn Met Gly Gly Arg Glu Ile Lys His Gly
225                 230                 235                 240

Val Ala Ile Ala Asp Ser Pro Leu Gly Pro Tyr Thr Lys Ser Glu Tyr
                245                 250                 255

Asn Pro Ile Thr Asn Ser Gly His Glu Val Ala Val Trp Pro Tyr Lys
            260                 265                 270
```

-continued

```
Gly Gly Met Ala Thr Met Leu Thr Thr Asp Gly Pro Glu Lys Asn Thr
        275                 280                 285

Cys Gln Trp Ala Glu Asp Gly Ile Asn Phe Asp Ile Met Ser His Ile
        290                 295                 300

Lys Gly Ala Pro Glu Ala Val Gly Phe Phe Arg Pro Glu Ser Asp Ser
305                 310                 315                 320

Asp Asp Pro Ile Ser Gly Ile Glu Trp Gly Leu Ser His Lys Tyr Asp
                325                 330                 335

Ala Ser Trp Asn Trp Asn Tyr Leu Cys Phe Phe Lys Thr Arg Arg Gln
            340                 345                 350

Val Leu Asp Ala Gly Ser Tyr Gln Gln Thr Gly Asp Ser Gly Ala Val
            355                 360                 365
```

METHOD FOR PURIFYING AND OBTAINING 3,6-ANHYDRO-L-GALACTOSE USING MICROORGANISMS

CROSS REFERENCE TO RELATED APPLICATION(S)

This application is a U.S. National Stage Application of International Application No. PCT/KR2017/003557, filed on Mar. 31, 2017, which claims the benefit under 35 USC 119(a) and 365(b) of Korean Patent Application No. 10-2016-0041058, filed on Apr. 4, 2016, in the Korean Intellectual Property Office.

BACKGROUND

1. Field of the Invention

The present invention relates to a novel method for purifying 3,6-anhydro-L-galactose using microorganisms which improve the production yield of 3,6-anhydro-L-galactose by using microorganisms in purification after enzymatic hydrolysis of agarose or agar.

2. Discussion of Related Art

The main polysaccharide constituting red algae is agarose, which is a polymer formed by alternately linking 3,6-anhydro-L-galactose (hereinafter, referred to as "AHG") and D-galactose by α-1,3-bonds and β-1,4-bonds. Among these constituents, AHG is a multifunctional high value-added material with anti-cariogenic and colon cancer preventing functions as well as cosmetic whitening and moisturizing functions. Therefore, techniques for efficiently producing and purifying AHG from agar or agarose, which is the main carbohydrate of red algae, are very important.

First, to produce AHG, conventionally, an agarooligosaccharide is obtained by pretreating agarose or agar with a week acid, an acetic acid or a neutral buffer, Tris-HCl buffer (pH 7.4), with a low concentration, and neoagarobiose is produced from the agarooligosaccharide through the enzyme reaction with an exo-type β-agarase II. However, at this time, there is a disadvantage of co-production of agarotriose as a by-product, and to degrade the agarotriose, it is necessary to introduce an additional enzyme such as an agarolytic β-galactosidase (ABG). Afterward, monosaccharides such as AHG and D-galactose may be obtained through the enzyme reaction of an α-neoagarobiose hydrolase (NABH) (see FIG. 1a). However, when acetic acid is used during the first step of this process, pretreatment, a large amount of salts is produced in a subsequent neutralizing step, and when a low concentration of a neutral buffer is used, a pretreatment reaction is performed at a high temperature (170° C.), and thus a high temperature and high-pressure reactor is required for mass production. In addition, during the pretreatment, AHG is excessively degraded into 5-hydroxymethylfurfural (5-HMF), which has a disadvantage of lowering an AHG production yield. Particularly, since acetic acid causes a rancid smell, when AHG is used as a cosmetic material, the rancid smell may become a problem. In addition, since, during the pretreatment, alpha bonds are preferentially cleaved, and thus an ABG enzyme degrading agarotriose which remains as a by-product in subsequent enzymatic saccharification has to be additionally used, the process can be more complicated.

Second, to date, for purification of AHG, two-step chromatography including silica gel chromatography and bio-gel p2 column chromatography for the final products of enzymatic hydrolysis, AHG and D-galactose, have been used. According to this method, a harmful organic solvent (that is, dichloromethane, chloroform, methanol, etc.) is used during the silica gel chromatography, and due to a large amount of AHG lost in the purification, the final AHG yield is reduced.

SUMMARY OF THE INVENTION

The present invention is directed to providing a novel method for purifying AHG using microorganisms to prevent AHG loss caused by purification during AHG production by purification after enzymatic hydrolysis of agarose or agar.

The present invention is also directed to providing a composition for producing AHG, which can improve a production yield of AHG using the above-described method.

To achieve the objects, the present invention provides a method for purifying 3,6-anhydro-L-galactose using microorganisms, the method including:

reacting a group of enzymes including a thermostable agarase represented by an amino acid sequence set forth in SEQ ID NO: 1, an exo-type agarase and an α-neoagarobiose hydrolase with agarose or agar as a substrate;

culturing a microorganism having an ability to metabolize galactose using a product obtained from the above reaction as a carbon source; and obtaining 3,6-anhydro-L-galactose from a culture of the microorganism.

The present invention provides a composition for producing 3,6-anhydro-L-galactose, which includes:

a group of enzymes including a thermostable agarase represented by an amino acid sequence set forth in SEQ ID NO: 1, an exo-type agarase and an α-neoagarobiose hydrolase; and a microorganism having an ability to metabolize galactose.

The present invention provides an effect of obtaining AHG with a high yield by reducing AHG loss because AHG is obtained without a separate purification process, which is conventionally performed, by degrading agarose or agar into galactose and AHG without chemical pretreatment, neutralization and treatment with an agarotriose hydrolase with respect to agarose or agar, which are conventionally performed, using a group of enzymes consisting of a thermostable agarase, an exo-type agarase and an α-neoagarobiose hydrolase.

DETAILED DESCRIPTION OF EXEMPLARY EMBODIMENTS

Figure 1A:
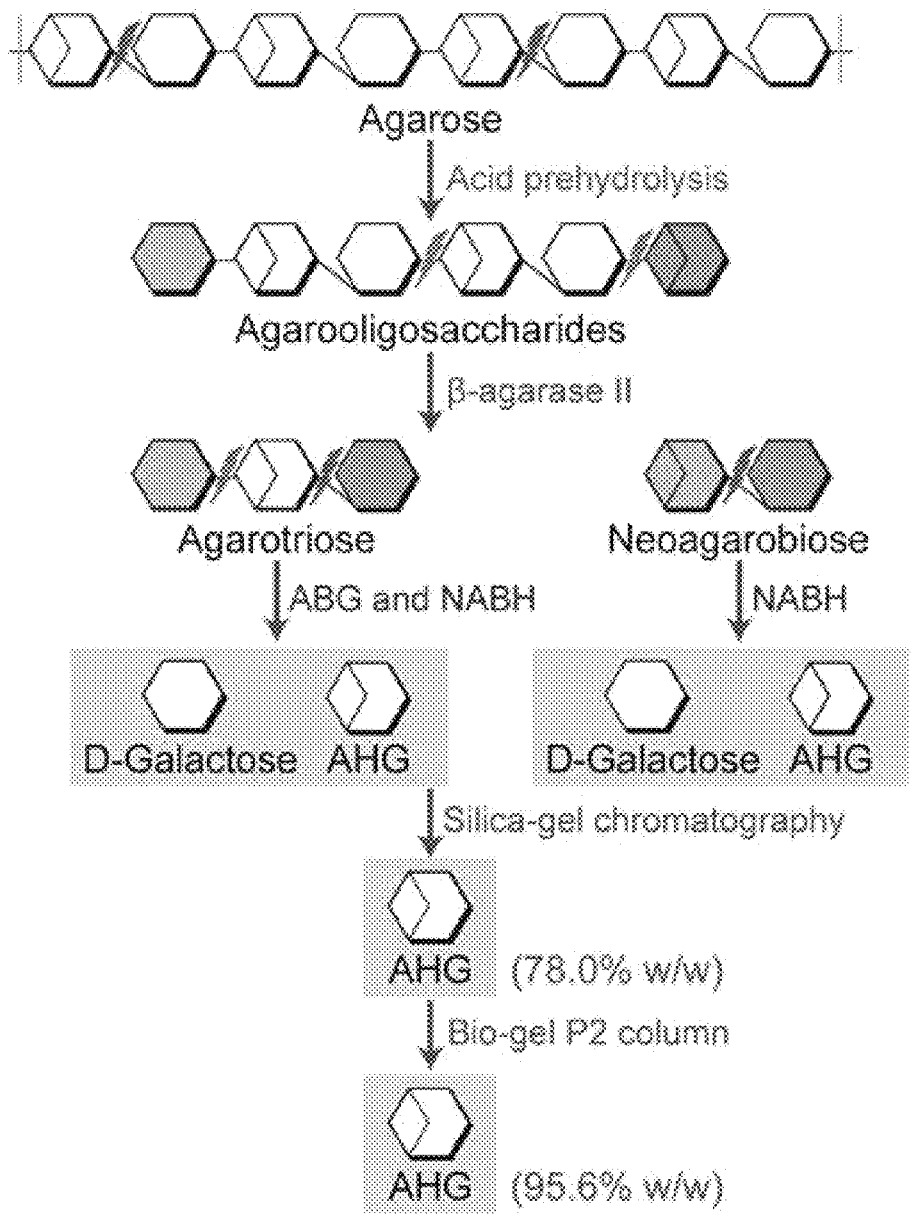
FIG. 1a is a schematic diagram illustrating AHG production from agarose through pretreatment with acetic acid and enzymatic saccharification and a purification process through two-step chromatography according to the conventional art.

Hereinafter, the composition of the present invention will be described in detail.

The present invention provides a method for purifying 3,6-anhydro-L-galactose using microorganisms, which includes:

reacting a group of enzymes including a thermostable agarase represented by an amino acid sequence set forth in SEQ ID NO: 1, an exo-type agarase and an α-neoagarobiose hydrolase with agarose or agar as a substrate;

culturing a microorganism having an ability to metabolize galactose using a product obtained from the above reaction as a carbon source; and obtaining 3,6-anhydro-L-galactose from a culture of the microorganism.

The present invention provides a composition for producing 3,6-anhydro-L-galactose, which includes:

a group of enzymes including a thermostable agarase represented by an amino acid sequence set forth in SEQ ID NO: 1, an exo-type agarase and an α-neoagarobiose hydrolase; and a microorganism having an ability to metabolize galactose.

Going one step further than conventionally-known pretreatment with acetic acid and hydrothermal pretreatment with a Tris-HCl buffer (pH 7.4), to solve the problems of the generation of salts in neutralization and a low saccharification yield caused by excessive degradation of AHG into 5-HMF during high temperature treatment, which are involved in pretreatment methods, the inventors developed a method for producing AHG and D-galactose with a high yield by degrading agarose or agar only through enzymatic saccharification using thermostable β-agarase Aga16B without chemical pretreatment by sequentially reacting three types of enzymes (Aga16B, Aga50D, NABH) with agarose or agar.

Such a process has the following advantages:

1) This process does not use expensive acetic acid and thus reduces costs. In addition, among the final degradation products, AHG is a material that can be used as a cosmetic functional material and does not use acetic acid causing a rancid smell, which is the one of the biggest advantages of the AHG.

2) A salt such as sodium acetate generated by neutralization is not generated.

3) Since an excessive degradation product such as 5-HMF is not generated, a monosaccharide production yield may be increased.

4) While a conventional chemical treatment process requires equipment such as a microwave, an enzyme process is performed at a low temperature and thus has an advantage for scale-up.

5) When three types of enzymes are used, agarotriose is not generated as a degradation product, and therefore, it is not necessary to use an agarotriose hydrolase.

Further, to prevent AHG loss during a conventional AHG purification process, the process is designed in such a way that only AHG is present in a hydrolysis product because galactose is metabolized using GRAS (Generally-Recognized-As-Safe) microorganisms which is safe for a human body and has an ability to metabolize galactose. Such a purification process does not use a harmful organic solvent and loses almost no AHG during purification. Therefore, purified AHG may be obtained with a high yield.

Figure 1B:
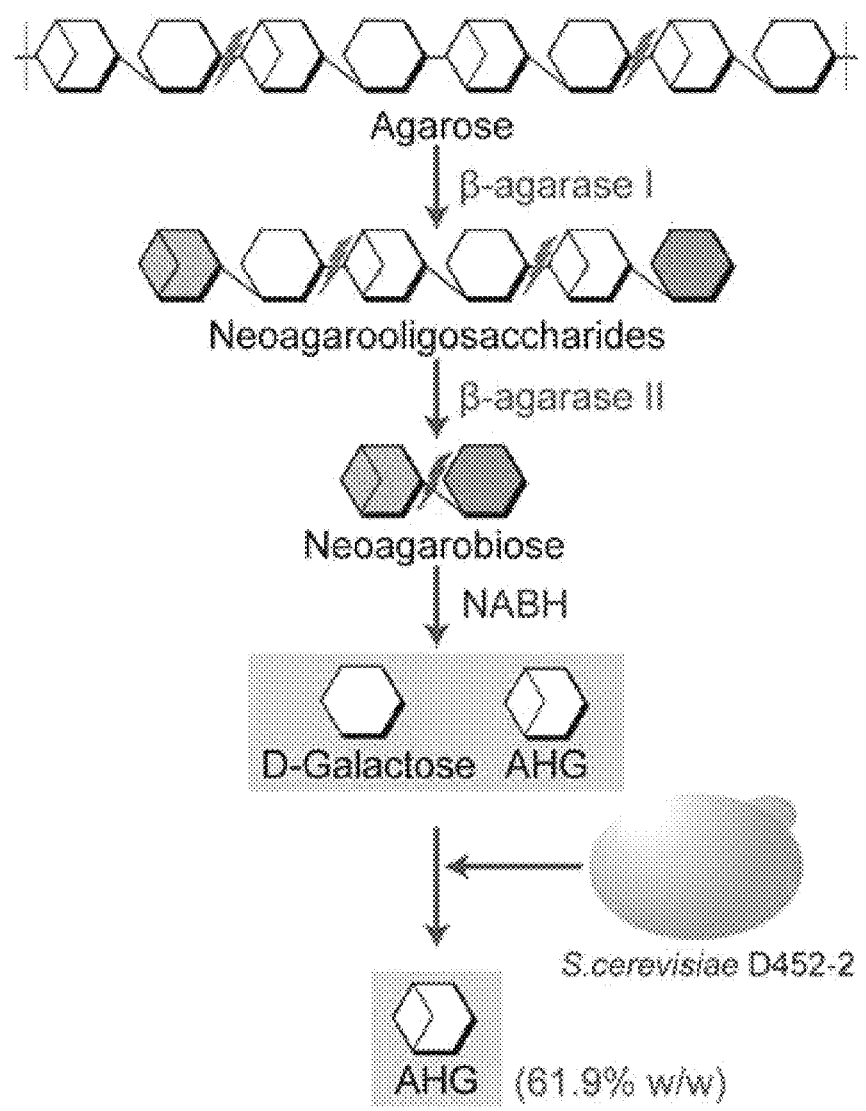
FIG. 1b is a schematic diagram illustrating AHG production through saccharification of agarose using microorganisms without pretreatment and an AHG purification process according to the present invention

Accordingly, a method for purifying 3,6-anhydro-L-galactose using microorganisms according to the present invention, as shown in FIG. 1b, may include:

enzymatically hydrolyzing agarose or agar without pretreatment; culturing a microorganism having an ability to metabolize galactose using the enzymatic hydrolysis product as a carbon source; and obtaining AHG through centrifugation or filtration of a culture of the microorganism.

The enzymatic hydrolysis of the agarose or agar may include:

reacting a thermostable agarase with agarose or agar; and reacting a product obtained from the above reaction with an exo-type agarase and an α-neoagarobiose hydrolase.

The thermostable agarase may be reacted with agarose or agar at a temperature ranging from 40° C. to 60° C. under a condition of 0 to 300 rpm, and a pH ranging from 5 to 9 for 30 minutes to 7 days, thereby producing neoagarotetraose or neoagarohexaose.

The thermostable agarase is an endo-type agarase, which maintains thermal stability from room temperature to 50° C. and has an activity of degrading agarose or agar from room temperature to 60° C. More specifically, the thermostable agarase exhibits optimal activity at approximately 55° C. Therefore, it can have activity at a temperature range in which agarose or agar is maintained in a liquid state, that is, approximately 35° C. or more.

The thermostable agarase uses agarose or agar as a substrate, and enzyme reaction products were identified as neoagarotetraose and neoagarohexaose having degrees of polymerization (DPs) of 4 to 6.

When an exo-type agarase, that is, an exo-type agarase and an α-neoagarobiose hydrolase are sequentially treated, the thermostable agarase may exhibit an improved saccharification yield compared to a saccharification yield obtained through the conventional chemical pretreatment. According to an exemplary embodiment, the saccharification yield was approximately 1.6-fold higher (72.5% of theoretical maximum) than the conventional buffer pretreatment.

The thermostable agarase may be transcribed and translated from a DNA fragment, that is, a coding gene, associated with the production of a polypeptide not only including upstream and downstream regions of the coding region of the enzyme, but also including an intron between individual coding fragments. For example, the thermostable agarase may be transcribed and translated from a sequence set forth in SEQ ID NO: 2, but the present invention is not particularly limited thereto. In addition, a protein having neoagarotetraose or neoagarohexaose hydrolytic activity as a mutant protein derived from the enzyme with one or more substitutions, deletions, translocations and additions, is also included in the scope of the enzyme of the present invention, and the protein preferably includes an amino acid sequence having at least 80%, 85%, 90%, 93%, 94%, 95%, 96%, 97%, 98%, or 99% sequence identity with the amino acid sequence set forth in SEQ ID NO: 1.

The thermostable agarase may be derived from *Saccharophagus degradans* 2-40$^T$, but the present invention is not particularly limited thereto.

The thermostable agarase may be isolated and purified from a supernatant of a *Saccharophagus degradans* 2-40$^T$ culture, or may be produced and isolated using a strain other than the *Saccharophagus degradans* 2-40$^T$ by a genetic-engineering recombination technique, or by an artificial, chemical synthesis method. When the recombination technique is used, the supernatant of *Saccharophagus degradans* 2-40$^T$ culture may be replaced with a supernatant of the transformed *E. coli* culture, but the present invention is not particularly limited thereto. According to an exemplary embodiment, the thermostable agarase may be obtained from *E. coli* transformed with a recombinant vector including the base sequence set forth in SEQ ID NO: 2 or a culture thereof.

The exo-type agarase may be an enzyme that degrades an agarooligosaccharide into neoagarobiose, which is a disaccharide, and agarotriose (D-galactose-β-1,4 bond-3,6-anhydro-L-galactose-α-1,3 bond-D-galactose), and an enzyme (hereinafter, also referred to as "Aga50D") that cleaves β-1,4-glycosidic bond between D-galactose and AHG of agarose.

The exo-type agarase may have an amino acid sequence set forth in SEQ ID NO:3, and in addition, a protein having agarooligosaccharide hydrolytic activity as a mutant protein derived from the enzyme with one or more substitutions, deletions, translocations and additions, is also included in the scope of the enzyme of the present invention. Preferably, the exo-type agarase includes the amino acid sequence set forth in SEQ ID NO:3, or an amino acid sequence having at least 80%, 85%, 90%, 93%, 94%, 95%, 96%, 97%, 98%, or 99% sequence identity with the sequence.

The exo-type agarase may be derived from *Saccharophagus degradans* 2-40$^T$, but the present invention is not particularly limited thereto.

The exo-type agarase may be isolated and purified from a supernatant of *Saccharophagus degradans* 2-40$^T$ culture, or from a strain other than the *Saccharophagus degradans* 2-40$^T$ by a genetic-engineering recombination technique, or may be produced and isolated by an artificial, chemical synthesis method.

When the recombination technique is used, factors used to facilitate conventional recombinant protein expression, for example, an antibiotic resistance gene, and a reporter protein or peptide which can be used in affinity column chromatography, may be used, and this technique is included in the range that can be easily embodied by those of ordinary skill in the art to which the present invention belongs. For example, the exo-type agarase from a supernatant of the culture of an edible, transformed strain, such as, transformed yeast cells may be used as an alternative. For a more specific preparation technique, Korean Unexamined Patent Application Publication Publication No. 2010-0040438 (Apr. 20, 2010) may be referenced.

The reaction between the agarooligosaccharide and the exo-type agarase may be performed at a temperature ranging from 20 to 40° C. for 30 to 7 days. More specifically, the reaction may be performed at a temperature ranging from 25 to 35° C. for 1 to 4 days.

The α-neoagarobiose hydrolase (referred to as SdNABH), which can degrade the neoagarobiose into AHG and D-galactose, may have an amino acid sequence set forth in SEQ ID NO: 4, and in addition, a protein having neoagarobiose hydrolytic activity as a mutant protein derived from the enzyme with one or more substitutions, deletions, translocations and additions, is also included in the scope of the enzyme of the present invention. The SdNABH preferably includes the amino acid sequence set forth in SEQ ID NO: 4, or an amino acid sequence having at least 80%, 85%, 90%, 93%, 94%, 95%, 96%, 97%, 98%, or 99% sequence identity with the sequence.

The α-neoagarobiose hydrolase may be derived from *Saccharophagus degradans* 2-40$^T$, but the present invention is not particularly limited thereto.

The α-neoagarobiose hydrolase may be isolated and purified from a supernatant of *Saccharophagus degradans* 2-40$^T$ culture, or from a strain other than the *Saccharophagus degradans* 2-40$^T$ by a genetic-engineering recombination technique, or may be produced and isolated by an artificial, chemical synthesis method. For a more specific preparation technique, Korean Unexamined Patent Application Publication No. 2013-0085017 (Jun. 26, 2013) may be referenced.

The reaction between the neoagarobiose and the α-neoagarobiose hydrolase may be performed at a temperature ranging from 20 to 40° C. for 30 minutes to 7 days. More specifically, the reaction may be performed at a temperature ranging from 25 to 35° C. for 1 to 4 days.

The "protein" and "polypeptide" used herein are used interchangeably.

In the present invention, the expression "a polypeptide has a specific percentage (e.g., 80%, 85%, 90%, 95% or 99%) of sequence identity with another sequence" means that, when two sequences are aligned and compared, the specific percentage of amino acid residues are the same. The alignment and percent homology or identity may be determined using suitable software programs known in the art, for example, the methods disclosed in the literature [CURRENT PROTOCOLS IN MOLECULAR BIOLOGY (F. M. Ausubel et al., (eds) 1987 Supplement 30 section 7.7.18)]. Preferable programs that can be used herein include the GCG Pileup program, FASTA (Pearson et al., 1988 *Proc.Natl Acad. Sci* USA 85:2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25:3389-3402). Another preferable alignment program is ALIGN Plus (Scientific and Educational Software, PA), preferably using basic parameters. Another available sequence software program is the TFASTA Data Searching Program available in Sequence Software Package Version 6.0 (Genetics Computer Group, University of Wisconsin, Madison, Wis.).

The term "recombinant" used herein means that, when being used in relation to a cell, nucleic acid, protein or vector, the cell, nucleic acid, protein or vector has been modified by introduction of a heterologous nucleic acid or protein or a change in an intrinsic nucleic acid or protein, or the cell is derived from a cell modified in such a manner. In other words, a recombinant cell expresses a gene which is not found in an intrinsic (non-recombinant) form of the cell, or alternatively, expresses an intrinsic gene which is abnormally expressed or never expressed.

The "nucleic acid" used herein encompasses single- or double-stranded DNA, RNA, and chemically-modified forms thereof. The "nucleic acid" and "polynucleotide" used herein can be used interchangeably. Due to the degeneracy of a genetic code, one or more codons may be used to encode a specific amino acid, and the present invention encompasses a polynucleotide encoding a specific amino acid sequence.

The term "introduction" used herein to describe the insertion of a nucleic acid sequence into a cell refers to "transfection," "transformation" or "transduction," and includes the description of incorporation of a nucleic acid sequence into a eukaryotic or prokaryotic cell. At this time, the nucleic acid sequence is incorporated into the genome of the cell (e.g., a chromosomal, a plasmid, a plastid or mitochondrial DNA), and thus is converted into an autonomous replicon, or transiently expressed.

In the method for purifying 3,6-anhydro-L-galactose using microorganisms of the present invention, microorganisms having an ability to metabolize galactose may be cultured using a degradation product of the neoagarobiose as a carbon source.

The microorganisms having an ability to metabolize galactose may be any one species selected from lactic acid bacteria including *Lactobacillus* and *Bifidobacterium* such as *L. casei, L. acidophilus, L. bulgaricus, B. longum, B. bifidum, Actiregularis*, etc.; *Bacillus; Streptomyces; Corynebacterium; Zymomonas* such as *Z. mobilis*, etc.; *E. coli*; and a yeast such as *Saccharomyces cerevisiae, P. pastoris*, etc. These are harmless GRAS microorganisms as described above and metabolize galactose, and therefore, only the microorganisms and AHG remain in the microbial culture.

Accordingly, AHG may remain in a liquid obtained after microorganisms or cell debris is removed through centrifugation or filtration of the microbial culture without a conventional purification process, resulting in AHG with a high yield.

Culture conditions for the microorganisms having an ability to metabolize galactose, for example, a culture medium, a culture temperature, time, etc. may be determined within the scope of understanding of one of ordinary skill in the art without particular limitation.

EXAMPLES

Hereinafter, the present invention will be described in further detail with reference to examples according to the present invention, but the scope of the present invention is not limited to the following examples.

<Example 1> Production of Aga16B, Aga50D and NABH Recombinant Enzymes

A gene of *Saccharophagus degradans* 2-40-derived endo-type β-agarase, Aga16B gene (Sde_1175), a gene of exo-type β-agarase, Aga50D gene, and a gene of neoagarobiose hydrolase, NABH gene, were introduced into *E. coli* BL21 (DE3) using a pET21a vector (for Aga50D, Korean Unexamined Patent Application Publication No. 2010-0040438 (Apr. 20, 2010), and for NABH, Korean Unexamined Patent Application Publication No. 2013-0085017 (Jun. 26, 2013)).

For Aga16B, the genome DNA was purified using a commercially available DNA kit (Bionia, Korea), and the Aga16B gene was amplified by PCR. Here, primers used herein were Aga16B-N, that is, 5'-AAA GGATCC ATGGCAGATTGGGACGGAATT-3' (Tm: 59.4); and Aga16B-C, that is, 5'-AAA GCGGCCGC GTTGCTAAGCGTGAACTTATCTA-3' (Tm: 59.3). A PCR product does not have a signal sequence located at amino acids 19-20 at the N-terminus of the Aga16B gene. As restriction enzymes, BamHI and NotI were used, and located at the 5' and 3' ends of the N- and C-termini. The PCR product and pET21a were double digested with BamHI and NotI, and the resulting DNA fragments were ligated using a T4 DNA ligase and transformed into *E. coli* BL21.

To pre-culture each gene-introduced recombinant *E. coli*, cells were cultured in a 50 mL conical tube containing 10 mL of LB broth containing 100 μg/mL of ampicillin at 37° C. for 9 hours. Afterward, 1 L of a main-culture with the same medium composition was inoculated with 10 mL of the pre-culture, and then when the cells were grown until the optical density detected using an optical density spectroscope reached a mid-exponential stage (OD 0.4 to 0.6), 0.1 mM isopropyl-β-di-thiogalactopyranoside (IPTG) was added, and then the cells were subjected to induction at 16° C. for 16 hours. Afterward, the cell culture was transferred to a 500 mL tube and centrifuged at 4° C. for 20 minutes at 10,000 rpm, thereby obtaining cells. To prevent the denaturation of a protein, the harvested cells were resuspended in 30 mL of Tris buffer (20 mM Tris-HCl, pH 7.4), and disrupted using a sonicator, resulting in cell lysis. Afterward, the lysate was centrifuged at 4° C. for 1 hour at 16,000 rpm. Proteins were purified using a HisTrap column (5 mL GE Healthcare), and the size of each purified protein was determined using a SDS-PAGE gel. A salt (imidazole) used for protein purification was removed using a desalting column. A concentration of the salt-removed recombinant protein enzyme was quantified by a BCA analysis method.

<Example 2> Enzyme Reactions of Aga16B, Aga50D and NABH

In the enzyme reaction of Aga16B, as a substrate, 5% (w/v) agarose was used, and the reaction was performed in a 20 mM Tris-HCl buffer (pH 7.4) at 55° C. and 200 rpm for 10 hours.

An Aga50D enzyme reaction was performed using an Aga16B enzyme reaction product, a neoagarooligosaccharide, as a substrate, under conditions of 25° C. and 200 rpm for 24 hours. Finally, the NABH enzyme reaction was performed using an Aga50D enzyme reaction product, neoagarobiose, as a substrate under conditions of 30° C. and 200 rpm for 12 hours.

After each enzyme reaction step, a reaction product was analyzed through thin layer chromatography (TLC). For the TLC analysis, 1 μl of the enzyme reaction product was loaded on a stationary phase silica gel plate, developed using n-butanol:ethanol:water (3:1:1 (v/v/v)) as a mobile-phase solvent for 1 hour, and then visualized using 10% sulfuric acid dissolved in ethanol and 0.2% 1,3-dihydroxynaphthalene dissolved in ethanol.

Figure 2:
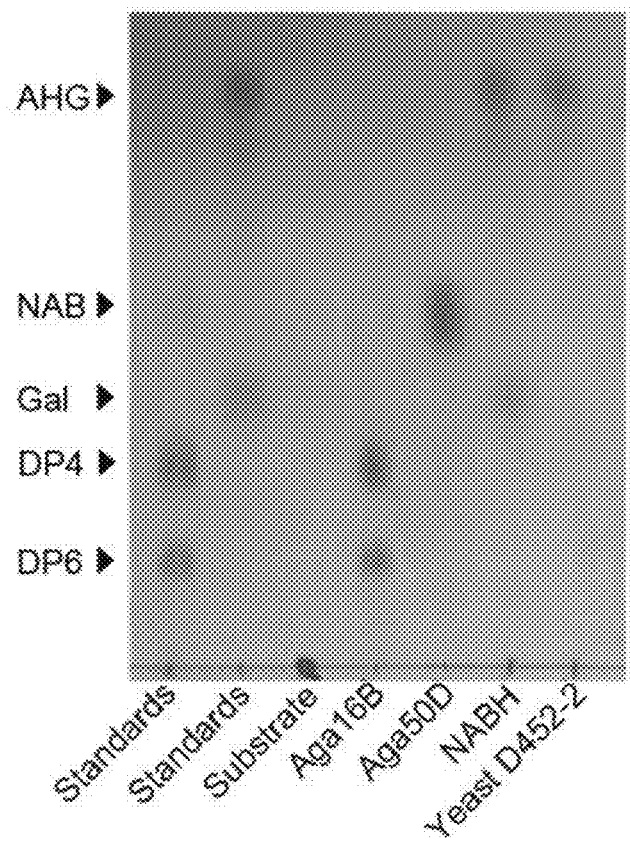
FIG. 2 is a TLC result illustrating AHG production from agarose by a three-step enzyme reaction and AHG purification using microorganisms according to the present invention

As shown in FIG. 2, an agarose substrate was degraded into a neoagarooligosaccharide through an enzyme reaction of endo-type β-agarase I, Aga16B, and at this time, the main products were neoagarotetraose and neoagarohexaose which have degrees of polymerization (DPs) of 4 to 6. Afterward, a disaccharide, neoagarobiose, was generated through an enzyme reaction of exo-type β-agarase II, Aga50D, and AHG and D-galactose were generated through an NABH enzyme reaction.

As a result of calculating production yields per each enzyme reaction step, since the reaction product of Aga16B is not a single material, it was impossible to quantify, and as a result of quantifying the Aga50D reaction product, neoagarobiose, 9.44 g of NAB was obtained from 10 g of agarose (0.944 g NAB/g agarose; Table 1). In addition, as a result of the NABH reaction, a monosaccharide yield obtained from 10 g of agarose was 7.52 g (0.752 g monomeric sugars/g agarose; Table 1).

TABLE 1

Production yields by steps in purification process using enzymatic saccharification and microorganism

| Step of purification process | Degradation product | Yield (based on initial agarose) (%, w/w) |
|---|---|---|
| Initial substrate | Agarose | 100.0 |
| Aga16B | Neoagarooligosaccharide (DP 4, 6) | NA |
| Aga50D | Neoagarobiose (DP 2) | 94.4 |
| NABH | AHG, galactose | 75.2 |
| Yeast | AHG | 37.3 |

NA: consisting of a mixture of DP4 + DP6 and difficult to calculate each yield

<Example 3> AHG Purification Using GRAS Microorganism, Yeast

The final reaction products obtained in Examples 1 and 2 are mainly AHG and D-galactose, and to remove D-galactose, yeast cells were cultured. The yeast used herein was the Saccharomyces cerevisiae D452-2 strain, and pre-culture was performed in YPD broth at 30° C. and 200 rpm for 24 hours. After the culture, a cell pellet was obtained by centrifugation at 5,000 rpm for 10 minutes and washed with Tris-HCl buffer (pH 7.4), and then centrifuged again under the same conditions, thereby obtaining a cell pellet.

For culture, the cell pellet of S. cerevisiae D452-2 was cultured in a minimal medium containing 3.35 g/L of a yeast nitrogen base and 0.4 g/L of CSM using the enzyme reaction products, which are AHG and D-galactose, as carbon sources. The cells were incubated at 30° C. and 200 rpm for 24 hours and then subjected to GC/MS analysis.

Figure 3A:
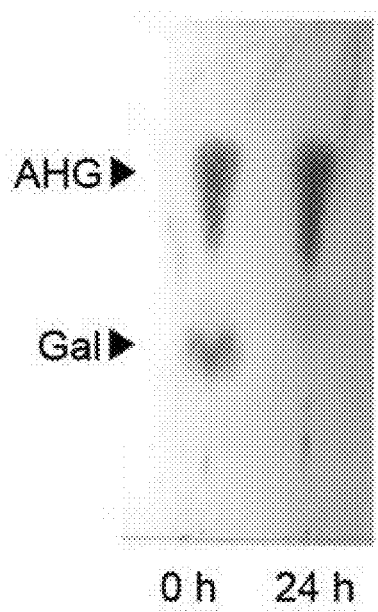
FIG. 3a shows TLC results of AHG purification before and after the culture of a GRAS microorganism, yeast.
Figure 3B:
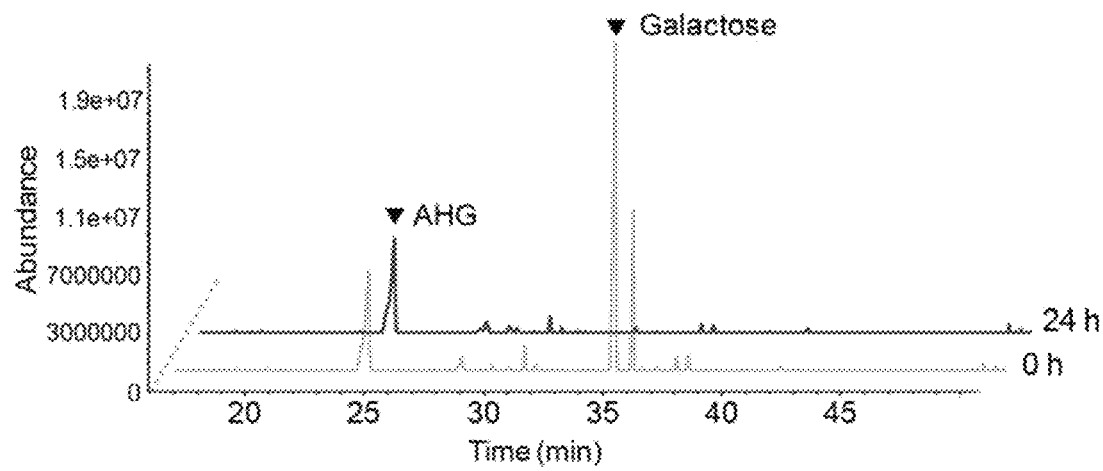
FIG. 3b shows GC/MS analysis results before and after the culture of the GRAS microorganism, yeast.

As shown in FIGS. 3a and 3b, it was confirmed that D-galactose was all consumed and only AHG remained, and as a result of calculating a yield, 3.73 g of purified AHG was obtained from 10 g of agarose (0.373 g of AHG/g agarose), and the AHG purity was 61.9% (w/w).

Figure 4A:
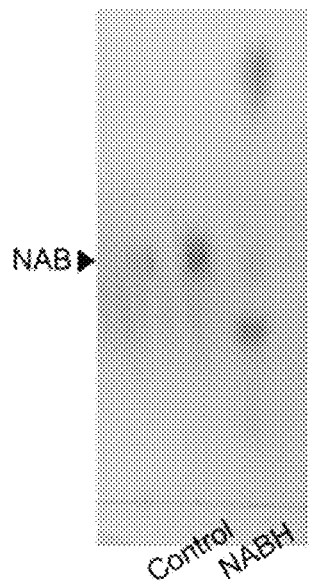
FIG. 4a shows a TLC analysis result obtained by measuring NABH activity of a NABH gene-introduced recombinant enzyme.
Figure 4B:
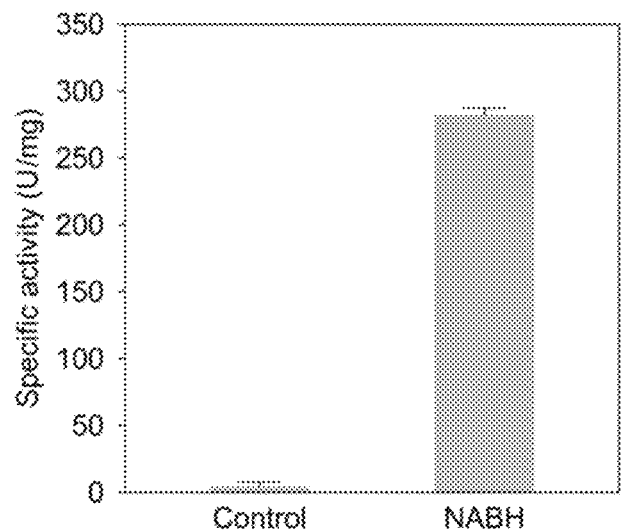
FIG. 4b shows a result of measuring NABH-specific activity of a NABH gene-introduced recombinant enzyme. Control represents empty vector-introduced *Saccharomyces serevisiae* D452-2, and NABH represents NABH-introduced *Saccharomyces serevisiae* D452-2.

<Example 4> Measurement of Enzyme Activity of NABH-Introduced Recombinant Yeast NABH NABH was cloned in a pRS425GPD vector (auxotrophic marker, Leu-) to be introduced into Saccharomyces cerevisiae D452-2, and activity was measured by in vitro analysis. The yeast cells harboring the NABH gene-containing plasmid were disrupted using a yeast protein extraction reagent (Y-PER), and a soluble protein was quantified through BCA analysis. A crude protein was subjected to a NABH enzyme reaction with a NAB substrate under conditions of 30° C. and 200 rpm. For qualitative analysis of the activity of the NABH enzyme, the reaction products were analyzed by TLC, thereby detecting the specific activity of NABH (FIGS. 4A and 4B).

<Example 5> AHG Purification Using NABH-Introduced Recombinant Yeast

The NABH enzyme activity of the NABH-introduced recombinant yeast was determined by Example 4. Accordingly, an experiment was carried out to purify AHG from a disaccharide, neoagarobiose, not from AHG and D-galactose. At this time, NABH-introduced recombinant yeast was cultured in a minimal medium containing 3.35 g/L of a yeast nitrogen base and 0.4 g/L of CSM (Leu-) using an Aga50D reaction product, neoagarobiose, as a carbon source. The yeast cells were incubated at 30° C. and 200 rpm, and the carbon source of the cell culture was observed over time.

Figure 5A:
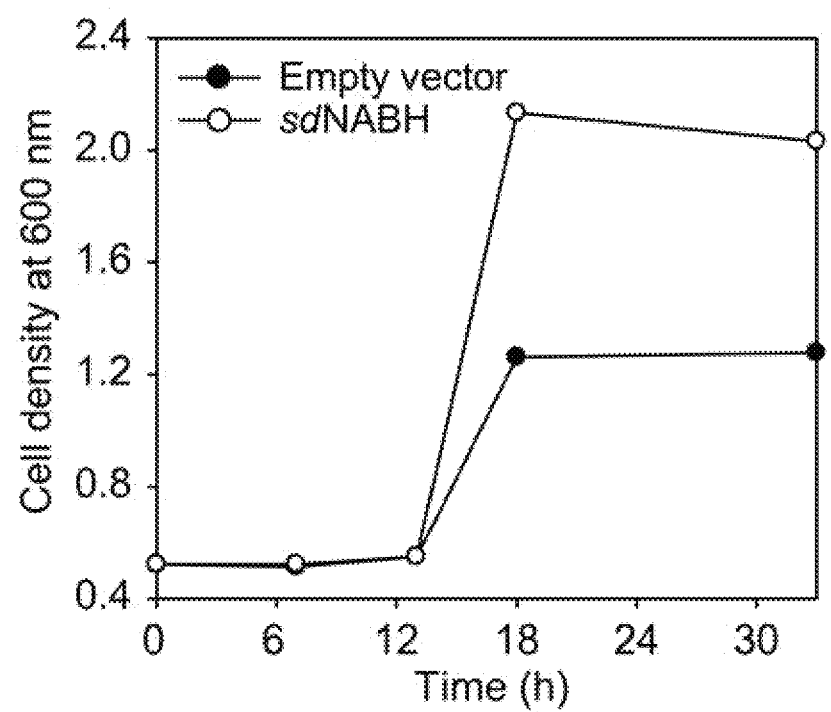
FIG. 5a shows a TLC analysis result illustrating time-dependent change in cell growth using a disaccharide, neoagarobiose, as a substrate.
Figure 5B:
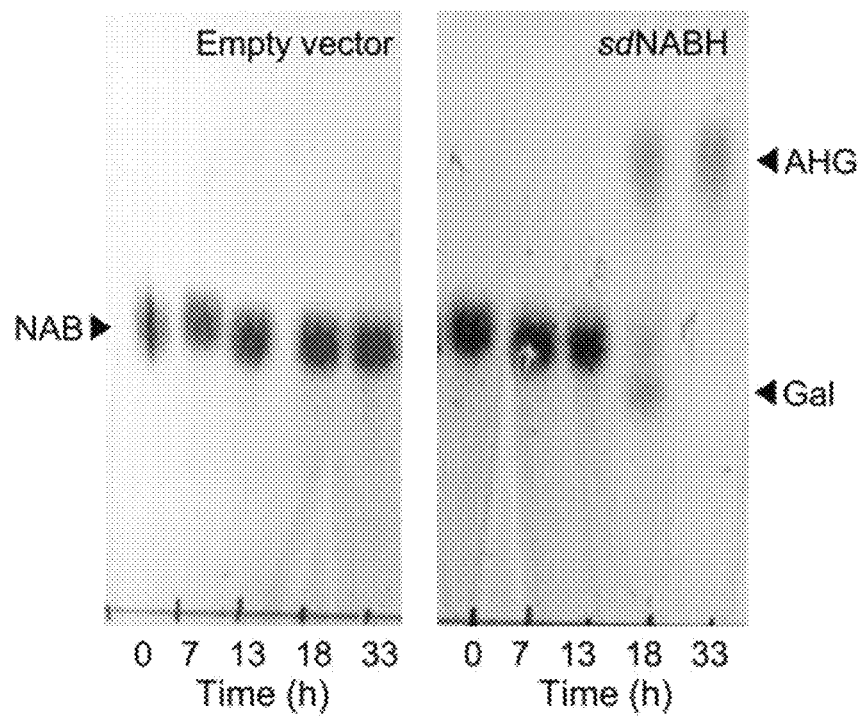
FIG. 5b shows a TLC analysis result illustrating time-dependent change in a carbon source in a medium using a disaccharide, neoagarobiose. Control represents empty vector-introduced *Saccharomyces serevisiae* D452-2, and NABH represents NABH-introduced *Saccharomyces cerevisiae* D452-2.

As shown in FIGS. 5a and 5b, it was observed that, as a control, the pRS425GPD vector-introduced recombinant yeast did not metabolize NAB, whereas not only the NABH-introduced recombinant yeast was grown by degrading NAB, thereby metabolizing galactose, but also AHG was released outside the cells.

Accordingly, using the NABH-introduced recombinant yeast, AHG may be purified from NAB.

<Example 6> Confirmation of AHG Purification Effect in Other Microorganisms Having D-Galactose Metabolism The final reaction products obtained in Examples 1 and 2 were mainly AHG and D-galactose, and AHG was purified using E. coli, P. pastoris, and Z. mobilis, which have a function of metabolizing D-galactose.

The E. coli used herein was the E. coli K12 strain, and pre-culture was performed in LB broth at 37° C. and 200 rpm for 16 hours. The strain of the species of the yeast genus Pichia used herein was P. pastoris X33, and pre-culture was performed in YPD broth at 30° C. and 200 rpm for 16 hours. The strain of the species of the gram-negative genus Zymomonas used herein was Z. mobilis ATCC 31821, and pre-culture was performed in an RM medium containing 100 mM potassium phosphate buffer (pH 6.0) at 30° C. and 200 rpm for 16 hours. After the culture, each cell pellet was obtained by centrifugation at 6,000 rpm for 20 minutes, washed with a Tris-HCl buffer (pH 7.4), and then centrifuged again under the same conditions, thereby obtaining a cell pellet.

For culture, a cell pellet of E. coli K12 was inoculated into a minimal medium containing 2.5 g/L of a yeast nitrogen base and 20 mM Tris-HCl buffer (pH 7.4) using enzyme reaction products, which are AHG and D-galactose, as carbon sources.

For culture, each of a cell pellet of P. pastoris X33 and a cell pellet of Z. mobilis ATCC 31821 was inoculated into a minimal medium containing 3.35 g/L of a yeast nitrogen base and 0.4 g/L of CSM using enzyme reaction products, which are AHG and D-galactose, as a carbon source. The cells were incubated at 30° C. and 200 rpm for 24 hours, and then qualitatively analyzed through TLC.

Figure 6A:
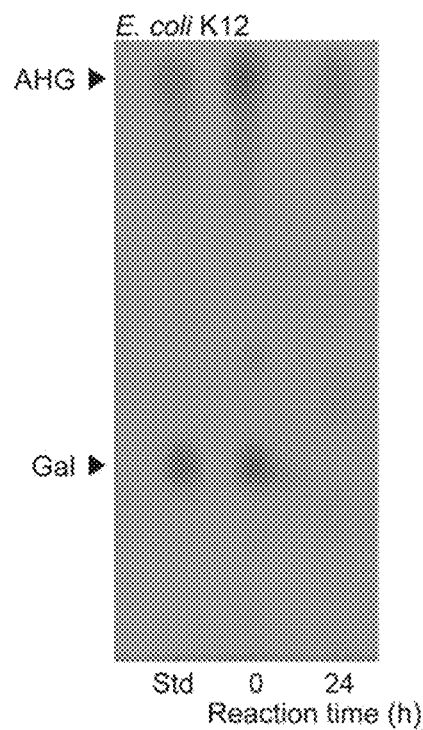
FIG. 6a shows an AHG purification result using *E. coli* having D-galactose metabolism.
Figure 6B:
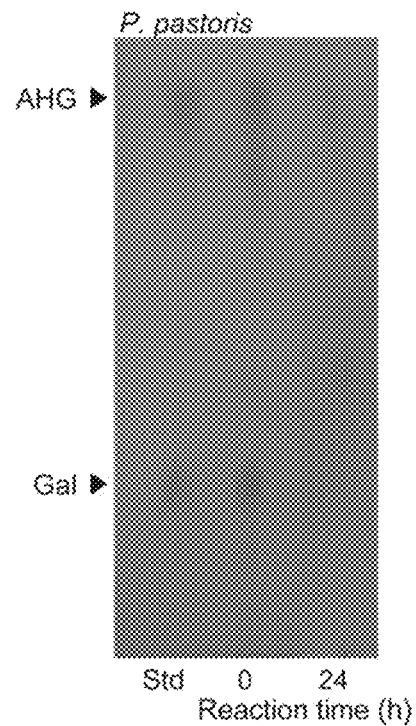
FIG. 6b shows an AHG purification result using *P. pastoris* having D-galactose metabolism.
Figure 6C:
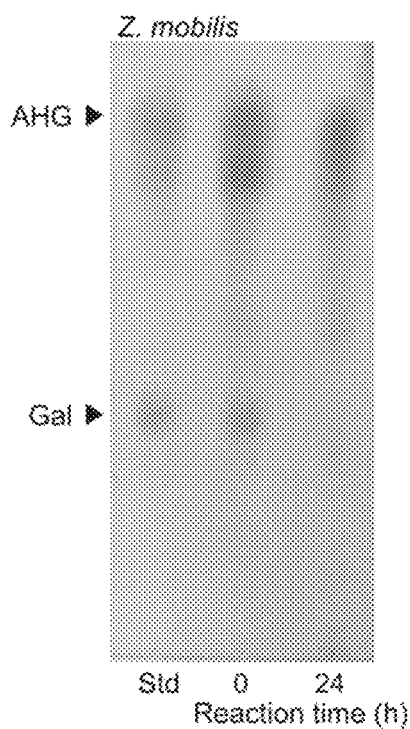
FIG. 6c shows an AHG purification result using *Z. mobilis* having D-galactose metabolism.

As shown in FIGS. 6a to 6c, it was confirmed that, after 24 hours, D-galactose was completely removed, and only AHG remained.

The present invention may be applied in the field of production of 3,6-anhydro-L-galactose.

What is claimed is:

1. A method for purifying and obtaining 3,6-anhydro-L-galactose using microorganisms, comprising:
    reacting agarose or agar with a thermostable agarase, an exo-type agarase, and an α-neoagarobiose hydrolase, sequentially without pretreatment of the agarose or agar;
    culturing a microorganism having an ability to metabolize galactose in a cell culture media comprising a product resulting from the reacting the agarose or agar with the thermostable agarase, the exo-type agarase, and the α-neoagarobiose hydrolase; and
    collecting 3,6-anhydro-L-galactose by centrifugating or filtering a culture of the microorganism,
    wherein the thermostable agarase comprises amino acid sequences of SEQ ID NO: 1, the exo-type agarase comprises amino acid sequences of SEQ ID NO: 3, and the α-neoagarobiose hydrolase comprises amino acid sequences of SEQ ID NO: 4,
    wherein the microorganism having an ability to metabolize galactose is selected from *Zymomonas mobilis* and *Pichia pastoris*, and
    wherein the reacting the agarose or agar with the thermostable agarase is performed at a temperature ranging from 40 to 60° C. under a condition of 0 to 300 rpm and a pH ranging from 5 to 9 for 30 minutes to 7 days.

2. The method according to claim 1, wherein a product resulting from the reacting the agarose or agar with the thermostable agarase is reacted with the exo-type agarase and the α-neoagarobiose hydrolase at a temperature ranging from 20 to 40° C., under a condition of 0 to 200 rpm, for 30 minutes to 7 days.

* * * * *